United States Patent [19]

Takayama et al.

[11] Patent Number: 5,091,155
[45] Date of Patent: Feb. 25, 1992

[54] ALCOHOL CONCENTRATION SENSOR

[75] Inventors: Hideto Takayama; Yoshihiro Tsuruoka; Takashi Matsuzawa; Hirao Nagae, all of Tokyo, Japan

[73] Assignees: Nemoto & Co., Ltd.; Toppan Printing Co., both of Tokyo, Japan

[21] Appl. No.: 425,631

[22] Filed: Oct. 23, 1989

[30] Foreign Application Priority Data

| Oct. 24, 1988 | [JP] | Japan | 63-267825 |
| Jul. 31, 1989 | [JP] | Japan | 1-198780 |
| Jul. 31, 1989 | [JP] | Japan | 1-198781 |
| Jul. 31, 1989 | [JP] | Japan | 1-198782 |
| Aug. 8, 1989 | [JP] | Japan | 1-203959 |
| Aug. 8, 1989 | [JP] | Japan | 1-203960 |

[51] Int. Cl.$^5$ .................. G01N 25/20; G01N 31/12
[52] U.S. Cl. ......................... 422/88; 422/78; 422/83; 422/84; 436/131; 436/132; 436/160; 436/900
[58] Field of Search ............ 436/132, 131, 900, 147, 436/160; 422/78, 83, 84, 88

[56] References Cited

U.S. PATENT DOCUMENTS

| 4,556,635 | 12/1985 | Hitzman et al. | 435/25 |
| 4,749,553 | 6/1988 | Lopez et al. | 422/84 |
| 4,869,873 | 9/1989 | Klein et al. | 422/78 |
| 4,971,911 | 11/1990 | Giles | 436/131 |

Primary Examiner—Robert J. Warden
Assistant Examiner—Lyle A. Alexander
Attorney, Agent, or Firm—Armstrong, Niakaido, Marmelstein, Kubovcik & Murray

[57] ABSTRACT

An alcohol concentration sensor provided a tube shaped means (21) of which the top end (211) is closed with a top end closing means (20) and of which the bottom end (212) is remained open, a gas supply tube means (22) which penetrates the top end closing means (20) to extend down into the tube shaped means (21), which is provided an air blower means (24), and of which the lower end (221) terminates slightly upper than the bottom end (212) of the tube shaped means (21), thereby the lower end (221) of the gas supply tube means (22) is soaked into a liquid (10) containing water and alcohol, of which the alcohol concentration is required to be determined, deeply sufficient to allow the air bubbles flown out of the gas supply tube means (22) into the liquid (10) to absorb sufficient quantity of alcohol contained in the liquid (10), whenever the tube shaped means (21) is soaked in the liquid (10), a gas drawing out means (26) which penetrates the top end closing means (20), a gas temperature sensing means (27) which is connected with the gas drawing out means (26) for determining the temperature of the gas in the neighborhood of a gas oxidation means for oxidizing the alcohol evaporated from the liquid (10), a temperature/alcohol concentration calibration means for calibrating the temperature of the gas toward the corresponding alcohol concentration, and an alcohol concentration output means for outputting the alcohol concentration determined by the temperature/alcohol concentration calibration means.

14 Claims, 14 Drawing Sheets

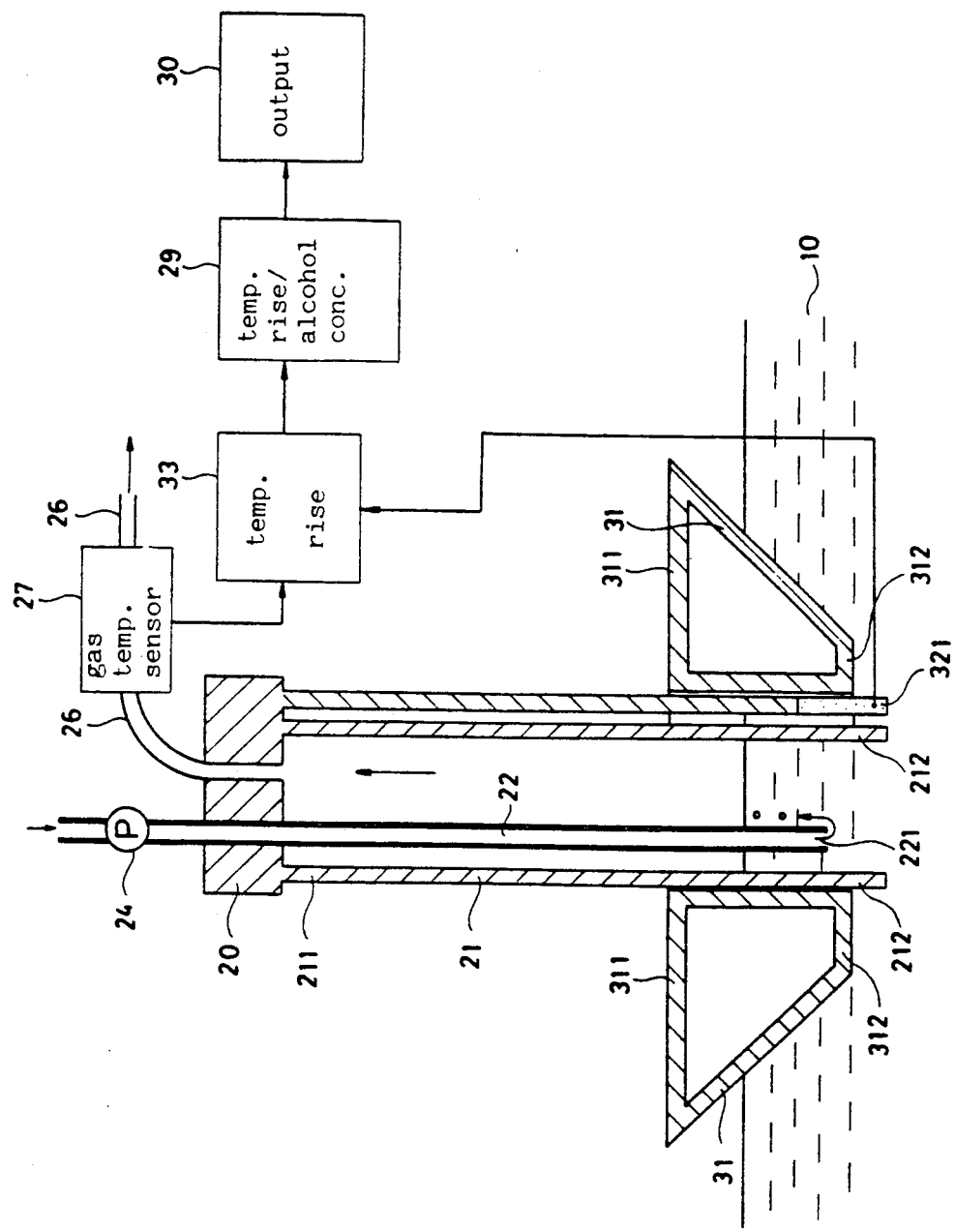

ALCOHOL CONCENTRATION SENSOR

FIELD OF THE INVENTION

This invention relates to an improvement applicable to an alcohol concentration sensor. Specifically, this invention relates to an improvement applicable to an alcohol concentration sensor which is employable for sensing the concentration of alcohol contained in a liquid containing water and alcohol e.g. an alcoholic beverage, fountain solution employable for lithographic printing method, or the like.

BACKGROUND OF THE INVENTION

It has been prevailingly required to determine the concentration of alcohol contained in a liquid containing water and ethyl alcohol, isopropyl alcohol, or the other alcohol, e.g. an alcoholic beverage, fountain solution employable for printing methods including a lithographic printing method, an offset printing method, or the like.

The most practical method for sensing the concentration of alcohol contained in a liquid containing water and alcohol is to employ a hydrostatic balance.

In addition to a method in which a hydrostatic balance is employed, employable is a method in which the specific gravity of the liquid containing water and alcohol is determined, after it is drawn to a vessel. However, this method is involved with a drawback in which this method is identified as a non-continuous one because some quantity of the liquid containing at least alcohol must be drawn to a vessel.

To remove this drawback, an alcohol concentration sensor which is illustrated in FIG. 1 was developed. Referring to the drawing, a vessel-like member 3 having an opening on one side thereof (the bottom side in the drawing) is held over a liquid 1 containing alcohol therein, remaining a closed space exposed to the natural surface of the liquid 1. The vessel-like member 3 is provided an inlet 2 through which the air is supplied into the closed space, an outlet 2 through which the mixture of the air and the vapor of alcohol is purged. A gas sensor 6 is provided to the vessel-like member 3 for sensing the concentration of alcohol contained in the mixture of the air and the vapor of the liquid confined in the vessel-like member 3.

When the foregoing improved alcohol concentration sensor is employed, the vapor remained in the closed space of the vessel-like member 3 is once purged by flowing the air through the inlet and outlet 2. After the closed space of the vessel-like member 3 is purged, a predetermined length of time (This length of time can be determined by conducting experiments for plural liquid mixtures having a variety of alcohol concentration.) is given to allow the liquid 1 to allow alcohol to evaporate to the extent where the alcohol concentration of the mixture of the air and alcohol vapor represents the alcohol concentration of the liquid 1 containing alcohol. Thereafter, the gas sensor 6 is employed to determine the concentration of alcohol contained in the mixture of the air and alcohol vapor confined in the closed space of the vessel-like member 3. Based on the results determined by employing the gas sensor 6, the concentration of alcohol contained in the liquid 1 containing alcohol is determined.

Therefore, a continuous measurement is impossible, even with the foregoing improved alcohol concentration sensor.

Incidentally, since the saturation vapor pressure of alcohol varies depending on the temperature of the vapor, the rate at which alcohol evaporates from the liquid 1 depends on the temperature of the vapor or of the liquid. This means that the concentration of alcohol determined to be contained in the mixture of alcohol vapor and the air, cannot precisely represent the concentration of alcohol contained in the liquid containing alcohol, even if such determination is conducted at a time when the aforementioned predetermined time has passed after the commencement of supply of the air into the closed space of the vessel-like member 3.

Therefore, for the purpose to remove the foregoing two independent drawbacks including (a) the batch type sensing is inevitable and (b) an error caused by variation of temperature of the vapor is inevitable, an alcohol concentration sensor which is capable of continuous measurement and which is provided with a means for correcting the error caused by the temperature of the mixture of the air and alcohol, was developed.

Referring to FIG. 2, a porous polymer tube 7 which exclusively allows volatile materials to pass, alcohol in this case, and prevents the other materials, water in this case, from passing through, and of which one end is connected with an air inlet tube 5 provided with an air supply pump 4 and of which the other end is connected with an outlet tube 5 provided with a gas sensor 6 therein. In addition, a thermometer 8 is provided, in the neighborhood of the above porous polymer tube 7.

When this more improved alcohol concentration sensor is employed, the porous polymer tube 7 is soaked in a liquid 1 containing alcohol, and the air is allowed to flow through the connected tube which is a connection of the inlet tube 5, the porous polymer tube 7 and the outlet tube 5, to allow alcohol contained in the liquid 1 containing alcohol to evaporate through the porous polymer tube 7. The gas sensor 6 senses the concentration of alcohol contained in the gas mixture containing the air and alcohol flown out of the porous polymer tube 7 to the outlet tube 5. The determined alcohol concentration is corrected, following the temperature determined by the thermometer 8.

The foregoing type alcohol concentration sensor sufficiently works exclusively for the liquid containing little volume of foreign materials e.g. the finished alcoholic beverage or the already brewed liqueur. On the contrary, if a sample liquid 1 contains insoluble foreign materials, as is in the case of a liqueur under brewing, a fountain water employable for a lithographic printing method, the foreign materials e.g. sludge produced during brewing or printing, etching solution which is added into fountain water for adjusting the pH amount thereof, covers the internal surface of the porous polymer tube 7, resultantly preventing alcohol from passing therethrough. This causes a drawback in which an error increases to a remarkable extent, following the employment of the alcohol concentration sensor. In other words, the longer the alcohol concentration sensor is employed, the larger the error becomes. Results of experiments indicate that an employment of the foregoing more improved alcohol concentration sensor for 40 days causes an increase in the error by approximately 10%.

Therefore, the objects of this invention is to provide a variety of alcohol concentration sensors which is capable of accurate and continuous measurement, even in cases where a liquid contains not only water and alcohol but also insoluble foreign materials, such measurement being possible for a long period with a high grade of accuracy, regardless of a variation of the temperature of the liquid and/or the ambient atmosphere, a variation of the resistance or the pressure of the liquid flow pass, a variation of the humidity of the gas mixture, a variation of the depth of the liquid, etc.

SUMMARY OF THE INVENTION

To achieve the foregoing objects of this invention, an alcohol concentration sensor in accordance with the first embodiment of this invention (as is shown in FIG. 3) is provided :

a tube shaped means (21) of which the top end (211) is closed with a top end closing member (20) and of which the bottom end (212) is remained open, a gas supply tube means (22) which penetrates the top end closing member (20) to extend down into the tube shaped means (21), which is provided an air blower means (24), and of which the lower end (221) terminates slightly upper than the bottom end (212) of the tube shaped means (21), thereby the lower end (221) of the gas supply tube means (22) is soaked into a liquid (10) containing water and alcohol, of which the alcohol concentration is required to be determined, deeply sufficient to allow the air bubbles flown out of the gas supply tube means (22) into the liquid (10) to absorb sufficient quantity of alcohol contained in a liquid (10), whenever the tube shaped means (21) is soaked in the liquid (10), a gas drawing out means (26) which penetrates the top end closing member (20), a gas temperature sensing means (27) which is connected with the gas drawing out means (26) for determining the temperature of the gas in the neighborhood of a gas oxidization means for oxidizing the alcohol evaporated from the liquid (10), a temperature/alcohol concentration calibration means for calibrating the temperature of the gas toward the corresponding alcohol concentration, and an alcohol concentration output means for outputting the alcohol concentration determined by the temperature/alcohol concentration calibration means.

The foregoing alcohol concentration sensor is innebitably involved with a drawback in which the determined alcohol concentration contains an error caused by a variation of the temperature of the liquid or the environmental atmosphere.

To remove this drawback, an alcohol concentration sensor in accordance with the second embodiment of this invention is provided:

a tube shaped means (21) of which the top end (211) is closed with the top end closing member (20) and of which the bottom end (212) is remained open, a gas supply tube means (22) which penetrates the top end closing member (20) to extend down into the tube shaped means (21), which is provided an air blower means (24), and of which the lower end (221) terminates slightly upper than the bottom end (212) of the tube shaped means (21), thereby the lower end (221) of the gas supply tube means (22) is soaked into a liquid (10) containing water and alcohol, of which the alcohol concentration is required to be determined, deeply sufficient to allow the air bubbles flown out of the gas supply tube means (22) into the liquid (10) to absorb sufficient quantity of alcohol contained in the liquid (10), whenever the tube shaped means (21) is soaked in the liquid (10), a gas drawing out means (26) which penetrates the top end closing member (20), a gas temperature sensing means (27) which is connected with the gas drawing out means (26) for determining the temperature of the gas in the neighborhood of a gas oxidization means for oxidizing the alcohol evaporated from the liquid (10), an air temperature sensing means for sensing the temperature of the environmental air, a gas temperature rise sensing means for determining the temperature rise of the gas in the neighborhood of the gas oxidization means against the ambient temperature determined by the gas temperature sensing means, a temperature rise/alcohol concentration calibration means for calibrating the temperature rise toward the corresponding alcohol concentration, and an alcohol concentration output means for outputting the alcohol concentration determined by the temperature rise/alcohol concentration calibration means.

To remove the above presented drawback (an error caused by a variation of temperature), an alcohol concentration sensor in accordance with the third embodiment of this invention (as is shown in FIG. 5) is provided: a tube shaped means (21) of which the top end (211) is closed with the top end closing member (20) and of which the bottom end (212) is remained open, a gas supply tube means (22) which penetrates the top end closing member (20) to extend down into the tube shaped means (21), which is provided an air blower means (24), and of which the lower end (221) terminates slightly upper than the bottom end (212) of the tube shaped means (21), thereby the lower end (221) of the gas supply tube means (22) is soaked into a liquid (10) containing water and alcohol, of which the alcohol concentration is required to be determined, deeply sufficient to allow the air bubbles flown out of the gas supply tube means (22) into the liquid (10) to absorb sufficient quantity of alcohol contained in the liquid (10), whenever the tube shaped means (21) is soaked in the liquid (10), a gas drawing out means (26) which penetrates the top end closing member (20), a gas temperature sensing means (27) which is connected with the gas drawing out means (26) for determining the temperature of the gas in the neighborhood of a gas oxidization means for oxidizing the alcohol evaporated from the liquid (10), a liquid temperature sensing means (32) which extends downward from the top end closing member (20) to the neighborhood of the lower end (221) of the tube shaped means (21) and which is provided a thermometer (321) at the lower end thereof, a gas temperature rise sensing means (45) for determining the temperature rise by comparing the gas temperature and the liquid temperature, a temperature rise/alcohol concentration calibration means for calibrating the temperature rise to the corresponding alcohol concentration, and an alcohol concentration output means for outputting the alcohol concentration determined by the temperature rise/alcohol concentration calibration means.

The foregoing alcohol concentration sensor is involved with a drawback in which the determined alcohol concentration contains an error caused by a variation of the resistance or the pressure of the liquid pass consisting of the tube shaped means (21) etc.

To remove this drawback, an alcohol concentration sensor in accordance with the fourth embodiment of this invention (as is shown in FIG. 6) is provided:

a tube shaped means (21) of which the top end (211) is closed with a top end closing member (20) and of which the bottom end (212) is remained open, a gas supply tube means (22) provided a flow stabilizing means (223) and which penetrates the top end closing member (20) to extend down into the tube shaped means (21), which is provided an air blower means (24), and of which the lower end (221) terminates slightly upper than the bottom end (212) of the tube shaped means (21), thereby the lower end (221) of the gas supply tube means (22) is soaked into a liquid (10) containing water and alcohol, of which the alcohol concentration is required to be determined, deeply sufficient to allow the air bubbles flown out of the gas supply tube means (22) into the liquid (10) to absorb sufficient quantity of alcohol contained in the liquid (10), whenever the tube shaped means (21) is soaked in the liquid (10).

The flow stabilizing means (223) generally could be a main valve (224) arranged in the gas supply tube means (22) proper or a combination of a main valve (224) arranged in the gas supply tube means (22) proper and an additional valve (225) arranged in a branch of the gas supply tube means (22).

The foregoing alcohol concentration sensor could be provided an air temperature sensing means for sensing the temperature of the environmental air, a gas temperature rise sensing means for determining the temperature rise of the gas in the neighborhood of the gas oxidization means with respect to the ambient temperature determined by the air temperature sensing means, a temperature rise/alcohol concentration calibration means for calibrating the temperature rise to the corresponding alcohol concentration.

Further, the foregoing alcohol concentration sensor could be provided a liquid temperature sensing means (32) which extends downward from the top end closing member (20) of the tube shaped means (21) to extend to the neighborhood of the lower end (221) of the tube shaped member (21) and which is provided a thermometer (321) at the lower end, a gas temperature rise sensing means (45) for determining the temperature rise by comparing the gas temperature and the liquid temperature, a temperature rise/alcohol concentration calibration means for calibrating the temperature rise to the corresponding alcohol concentration.

To remove the drawback identical to that for the fourth embodiment, an alcohol concentration sensor in accordance with fifth embodiment of this invention (as is shown in FIG. 8) is provided:

a tube shaped means (21) of which the top end (211) is closed with a top end closing member (20) and of which the bottom end (212) is remained open, a gas supply tube means (22) which penetrates the top end closing member (20) to extend down into the tube shaped means (21), which is provided an air blower means (24), and of which the lower end (221) terminates slightly upper than the bottom end (212) of the tube shaped means (21), thereby the lower end (221) of the gas supply tube means (22) is soaked into a liquid (10) containing water and alcohol, of which the alcohol concentration is required to be determined, deeply sufficient to allow the air bubbles flown out of the gas supply tube means (22) into the liquid (10) to absorb sufficient quantity of alcohol contained in the liquid (10), whenever the tube shaped means (21) is soaked in the liquid (10), a gas drawing out means (26) which penetrates the top end closing member (20), a gas flow sensing means (261), a gas flow regulation means (31) which compares the gas flow determined by the gas flow sensing means (261) and a predetermined reference (34), a gas temperature sensing means (27) which is connected with the gas drawing out means (26) for determining the temperature of the gas in the neighborhood of a gas oxidization means for oxidizing the alcohol evaporated from the liquid (10), an ambient temperature sensing means (25) for sensing the temperature of the environmental air, a gas temperature rise sensing means (28) for determining the temperature rise of the gas in the neighborhood of the gas oxidization means against the ambient temperature determined by the gas temperature sensing means (25), a temperature rise/alcohol concentration calibration means (29) for calibrating the temperature rise to the corresponding alcohol concentration, an alcohol concentration output means (30) for outputting the alcohol concentration determined by the temperature/alcohol concentration calibration means (29).

Since this alcohol concentration sensor is provided an air temperature sensing means (25) for sensing the temperature of the environmental air, a gas temperature rise sensing means (28) for determining the temperature rise of the gas in the neighborhood of the gas oxidization means, a temperature rise/alcohol concentration calibration means (29) for calibrating the temperature rise to the corresponding alcohol concentration, the accuracy is excellent.

Further, to remove the drawback identical to those for the fourth and fifth embodiments, an alcohol concentration sensor in accordance with sixth embodiment of this invention (as is shown in FIG. 9) is provided: a tube shaped means (21) of which the top end (211) is closed with a top end closing member (20) and of which the bottom end (212) is remained open, a gas supply tube means (22) which penetrates the top end closing member (20) to extend down into the tube shaped means (21), which is provided an air blower means (24), and of which the lower end (221) terminates slightly upper than the bottom end (212) of the tube shaped means (21), thereby the lower end (221) of the gas supply tube means (22) is soaked into a liquid (10) containing water and alcohol, of which the alcohol concentration is required to be determined, deeply sufficient to allow the air bubbles flown out of the gas supply tube means (22) into the liquid (10) to absorb sufficient quantity of alcohol contained in the liquid (10), whenever the tube shaped means (21) is soaked in the liquid (10), a gas drawing out means (26) which penetrates the top end closing member (20), a gas flow sensing means (261), a gas flow regulation means (31) which compares the gas flow determined by the gas flow sensing means (261) and a predetermined reference 34), a gas temperature sensing means (27) which is connected with the gas drawing out means (26) for determining the temperature of the gas in the neighborhood of a gas oxidization means for oxidizing the alcohol evaporated from the liquid (10), a liquid temperature sensing means (32) which extends downward from the top end closing member (20) to extend to the neighborhood of the lower end (221) of the tube shaped member (21) and which is provided a thermometer (321) at the lower end thereof, a gas temperature rise sensing means (33) for determining the temperature rise by comparing the gas temperature determined by the gas temperature sensing means (27) and the liquid temperature determined by the thermometer (321), a temperature rise/alcohol concentration calibration means (29) for calibrating the temperature rise to the corresponding alcohol concentration, and an alcohol concentration output means (30) for outputting the alcohol concentration determined by the temperature/alcohol concentration calibration means.

The foregoing alcohol concentration sensor is involved with a drawback in which the determined alcohol concentration contains an error caused by an unstable flow caused by explosion of the air bubbles at the surface of the liquid (10).

To remove this drawback, an alcohol concentration sensor in accordance with the seventh embodiment of this invention (as is shown in FIG. 10) is provided: a tube shaped means (21) of which the top end (211) is closed with a top end closing member (20) and of which the bottom end (212) is remained open, a gas supply tube means (22) which penetrates the top end closing member (20) to extend down into the tube shaped means (21), which is provided an air blower means (24), and of which the lower end (221) terminates slightly upper than the lower end of (212) of the tube shaped means (21), thereby the lower end (221) of the gas supply tube means (22) is soaked into a liquid (10) containing water and alcohol, of which the alcohol concentration is required to be determined, deeply sufficient to allow the air bubbles flown out of the gas supply tube means (22) into the liquid (10) to absorb sufficient quantity of alcohol contained in the liquid (10), whenever the tube shaped means (21) is soaked in the liquid (10), a gas drawing out means (26) which penetrates the top end closing member (20) and which is provided a filter (40) for filtering water particles, a gas temperature sensing means (27) which is arranged in the gas drawing out means (26) for determining the temperature of the gas in the neighborhood of a gas oxidization means for oxidizing the alcohol evaporated from the gas mixture containing alcohol and the air, a temperature/alcohol concentration calibration means for calibrating the temperature to the corresponding alcohol concentration, and an alcohol concentration output means for outputting the alcohol concentration determined by the temperature/alcohol concentration calibration means.

This alcohol concentration sensor could be provided a gas temperature sensing means (25) for sensing the temperature of the environmental air, a gas temperature rise sensing means (28) for determining the temperature rise of the gas in the neighborhood of the gas oxidization means, a temperature rise/alcohol concentration calibration means (29) for calibrating the temperature rise to the corresponding alcohol concentration, as is illustrated in FIG. 8.

This alcohol concentration sensor could be provided a liquid temperature sensing means (32) which extends downward from the top end closing member (20) of the tube shaped means (21) to reach to the neighborhood of the lower end (221) of the tube shaped member (21) and which is provided a thermometer (321) at the lower end, a gas temperature rise sensing means (33) for determining the temperature rise by comparing the gas temperature and the liquid temperature, a temperature rise/alcohol concentration calibration means (29) for calibrating the temperature rise to the corresponding alcohol concentration, as is illustrated in FIG. 9.

The foregoing alcohol concentration sensor is involved with a drawback in which the gas sensor is not necessarily durable particularly against humidity.

To remove this drawback, an alcohol concentration sensor in accordance with the eighth embodiment of this invention (as is shown in FIG. 11) is provided:

a tube shaped means (21) of which the top end (211) is closed with a top end closing member (20) and of which the bottom end (212) is remained open, a gas supply tube means (22) which penetrates the top end closing member (20) to extend down into the tube shaped means (21), which is provided an air blower means (24), and of which the lower end (221) terminates slightly upper than the lower end of (212) of the tube shaped means (21), thereby the lower end (221) of the gas supply tube means (22) is soaked into a liquid (10) containing water and alcohol, of which the alcohol concentration is required to be determined, deeply sufficient to allow the air bubbles flown out of the gas supply tube means (22) into the liquid (10) to absorb sufficient quantity of alcohol contained in the liquid (10), whenever the tube shaped means (21) is soaked in the liquid (10), a gas drawing out means (26) which penetrates the top end closing member (20), a gas temperature sensing means (27) which is arranged in the gas drawing out means (26) and which is protected by a porous film (41) which allows the air to pass through but prevents water from passing through and is resistive against heat.

This alcohol concentration sensor could be provided an air temperature sensing means (25) for sensing the temperature of the environmental air, a gas temperature rise sensing means (28) for determining the temperature rise of the gas in the neighborhood of the gas oxidization means, a temperature rise/alcohol concentration calibration means (29) for calibrating the temperature rise to the corresponding alcohol concentration, as is illustrated in FIG. 8.

This alcohol concentration sensor could be provided a liquid temperature sensing means (32) which extends downward from the top end closing member (20) of the tube shaped means (21) to reach to the neighborhood of the lower end (221) of the tube shaped member (21) and which is provided a thermometer (321) at the lower end, a gas temperature rise sensing means (33) for determining the temperature rise by comparing the gas temperature and the liquid temperature, a temperature rise/alcohol concentration calibration means (29) for calibrating the temperature rise to the corresponding alcohol concentration, as is illustrated in FIG. 9.

The foregoing alcohol concentration sensor is involved with a drawback in which the foregoing alcohol concentration sensor cannot be employed, whenever the depth of the liquid of which the alcohol concentration is examined, is too deep.

To remove this drawback, an alcohol concentration sensor in accordance with the ninth embodiment of this invention (as is shown in FIG. 12) is provided:

a tube shaped means (21) of which the top end (211) is closed with a top end closing member (20) and of which the bottom end (212) is remained open, a gas supply tube means (22) which penetrates the top end closing member (20) to extend down into the tube shaped means (21), which is provided an air blower means (24), and of which the lower end (221) terminates slightly upper than the bottom end (212) of the tube shaped means (21), thereby the lower end (221) of the gas supply tube means (22) is soaked into a liquid (10) containing water and alcohol, of which the alcohol concentration is required to be determined, deeply sufficient to allow the air bubbles flown out of the gas supply tube means (22) into the liquid (10) to absorb sufficient quantity of alcohol contained in the liquid (10), whenever the tube shaped means (21) is soaked in the liquid (10), a gas drawing out means (26) which penetrates the top end closing member (20), a gas temperature sensing means (27) which is connected with the gas drawing out means (26) for determining the temperature of the gas in the neighborhood of a gas oxidization means for oxidizing the alcohol evaporated from the liquid (10), an ambient temperature sensing means (25) for sensing the temperature of the environmental air, a gas temperature rise sensing means (28) for determining the temperature rise of the gas in the neighborhood of the gas oxidization means against the ambient temperature determined by the air temperature sensing means (25), a temperature rise/alcohol concentration calibration means (29) for calibrating the temperature rise to the corresponding alcohol concentration, an alcohol concentration output means (30) for outputting the alcohol concentration determined by the temperature/alcohol concentration calibration means (29), and a float (41) arranged surrounding the tube shaped means (21).

The length of the external upper edge (421) could be larger than the length of the internal lower edge (422), as shown in FIG. 13 for the purpose to enhance the dynamical stability or the force of restitution.

The foregoing alcohol concentration sensor is not necessarily satisfactory from the view points of the temperature correction.

To improve the temperature correction, an alcohol concentration sensor in accordance with the tenth embodiment of this invention (as is shown in FIG. 14) is provided:

a tube shaped means (21) of which the top end (211) is closed with a top end closing member (20) and of which the bottom end (212) is remained open, a gas supply tube means (22) which penetrates the top end closing member (20) to extend down into the tube shaped means (21), which is provided an air blower means (24), and of which the lower end (221) terminates slightly upper than the bottom end (212) of the tube shaped means (21), thereby the lower end (221) of the gas supply tube means (22) is soaked into a liquid (10) containing water and alcohol, of which the alcohol concentration is required to be determined, deeply sufficient to allow the air bubbles flown out of the gas supply tube means (22) into the liquid (10) to absorb sufficient quantity of alcohol contained in the liquid (10), whenever the tube shaped means (21) is soaked in the liquid (10), a gas drawing out means (26) which penetrates the top end closing member (20), a gas temperature sensing means (27) which is connected with the gas drawing out means (26) for determining the temperature of the gas in the neighborhood of a gas oxidization means for oxidizing the alcohol evaporated from the liquid (10), a liquid temperature sensing means (32) which extends downward from the top end closing member (20) to the neighborhood of the lower end (221) of the tube shaped means (21) and which is provided a thermometer (321) at the lower end thereof, a gas temperature rise sensing means (33) for determining the temperature rise by comparing the gas temperature and the liquid temperature, a temperature rise/alcohol concentration calibration means (29) for calibrating the temperature rise to the corresponding alcohol concentration, an alcohol concentration output means for outputting the alcohol concentration determined by the temperature rise/alcohol concentration calibration means (30), and a float (31) arranged surrounding the tube shaped means (21).

The length of the external upper edge (311) could be larger than the length of the internal lower edge (312), as shown in FIG. 15 for the purpose to enhance the dynamical stability or the force of restitution.

BRIEF DESCRIPTION OF THE DRAWINGS

FIG. 15 is a modification of the tenth embodiment of this invention.

DETAILED DESCRIPTION OF PREFERRED EMBODIMENTS

FIRST EMBODIMENT

Figure 1:
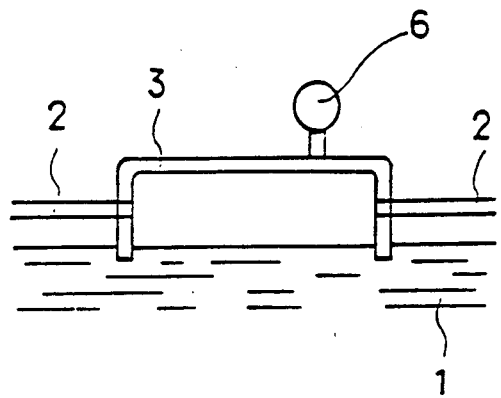
FIG. 1 is an alcohol concentration sensor available in the prior art.
Figure 2:
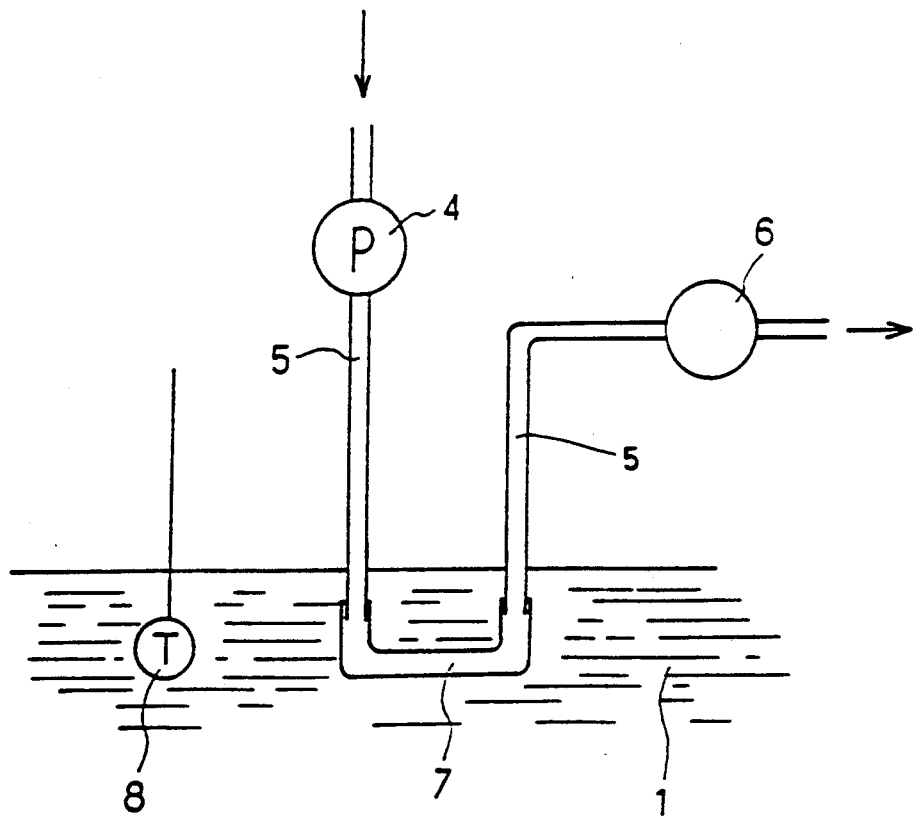
FIG. 2 is a continuous alcohol concentration sensor available in the prior art.
Figure 3:
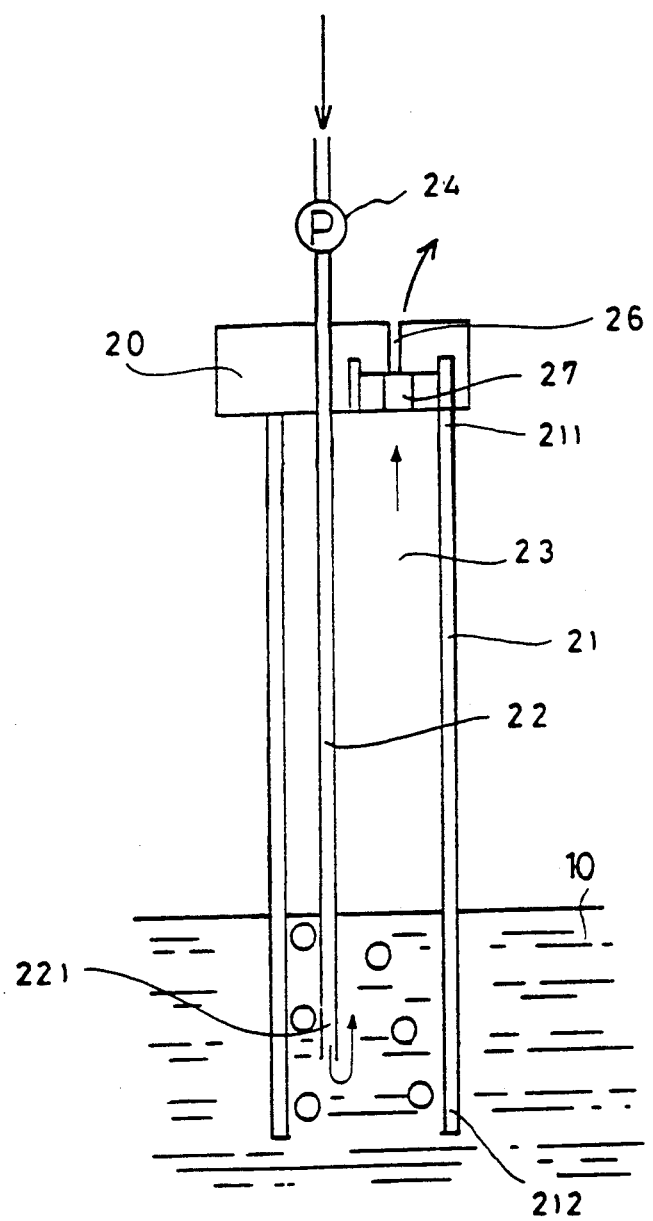
FIG. 3 is an alcohol concentration sensor in accordance with the first embodiment of this invention.

Referring to FIG. 3 which illustrates an alcohol concentration sensor in accordance with the first embodiment of this invention, the top end 211 of a tube shaped means 21 is closed with a top end closing means 20 and the bottom end 212 thereof is remained open, remaining an open space 23 therebetween. The bottom end 212 is soaked in the water 10 containing alcohol of which the alcohol concentration is examined. An air supply tube 22 which is provided with a blower 24 penetrates the top end closing means 20 to extend into the water 10 containing alcohol. A gas sensor 27 is arranged in the top end closing means 20 to allow the gas mixture of the air and alcohol vapor flown out of the open space 23 of the tube shaped means 21 through an opening 26.

The tube shaped means 21 has no limitations for the shape and the material, provided it hardly rusts and is durable against alcohol. The air supply tube 22 is required to have a length which allows the air flown therethrough is released in the water 10 in the form of bubbles which are allowed a time enough to allow the alcohol contained therein to evaporate into the water 10, during the time in which the bubbles rise up to the open space 23. Needless to emphasize, the length of the air supply tube 22 is slightly shorter than that of the tube shaped means 21 not to allow the bubbles to escape out of the tube shaped means 21.

The gas sensor 27 can be of a catalytic type thermometer, a semiconductor type thermometer, or the like, which determines a temperature caused by oxidization of the alcohol contained in the mixture of the air and alcohol supplied in the neighborhood of the gas sensor 27. Provided the gas sensor 27 is designed to indicate the temperature in terms of the corresponding alcoholic concentration contained in the mixture of the air and alcohol supplied in the neighborhood of the gas sensor 27, it is possible to determine the alcoholic concentration of the gas mixture, resultantly being capable of sensing the concentration of the alcohol contained in the liquid or the water 10. Thermometers having such characteristics are available in the prior art. For example, such thermometers are based on a table look up system or are made by employing microcomputer or the like.

When being employed, this alcoholic concentration sensor is soaked in the water 10 containing alcohol in the manner that the air supply tube 22 is also soaked with a depth enough to allow the bubbles flown therefrom to use a length of time to absorb alcohol contained in the water 10.

Following the function of the blower 24, the air is flown into the water out of the air supply tube 22, and flows upward into the open space 23 in the form of bubbles. During this period, the bubbles absorb alcohol contained in the water 10, resultantly allowing the concentration of alcohol contained in the mixture of the air and alcohol to be proportional to the concentration of the water 10 containing alcohol.

Following the supply of the air flown out of the air supply tube 22, the mixture of the air and alcohol flows out of the open space 23 into the gas sensor 27, which determines the alcohol concentration of the mixture of the air and alcohol flows out of the open space 23 through the opening 26.

It is thus needless to say that various means e.g. an alarm means, a negative feedback system which functions to maintain the alcohol concentration contained in the water 10 at a preferable value, or the like, is allowed to accompany the alcohol concentration sensor in accordance with this embodiment.

Since the foregoing alcohol concentration sensor has no members which are disturbed its continuous function, even if the water 10 contains insoluble foreign materials, the foregoing alcohol concentration sensor is durable against various insoluble foreign materials to be contained in the water 10 to be examined.

Further, since the foregoing alcohol concentration sensor utilizes compulsory evaporation based on the bubbling phenomenon of the air, a smaller dimension is allowed for the foregoing alcohol concentration sensor in accordance with this invention, in addition to an advantage in which the regulation of evaporation rate is easy and the measurement of the alcoholic concentration can be conducted in a continuous manner.

Further, since the tube shaped means 20 is soaked in the water, accurate measurement is allowed, even if the water is flowing.

Figure 4:
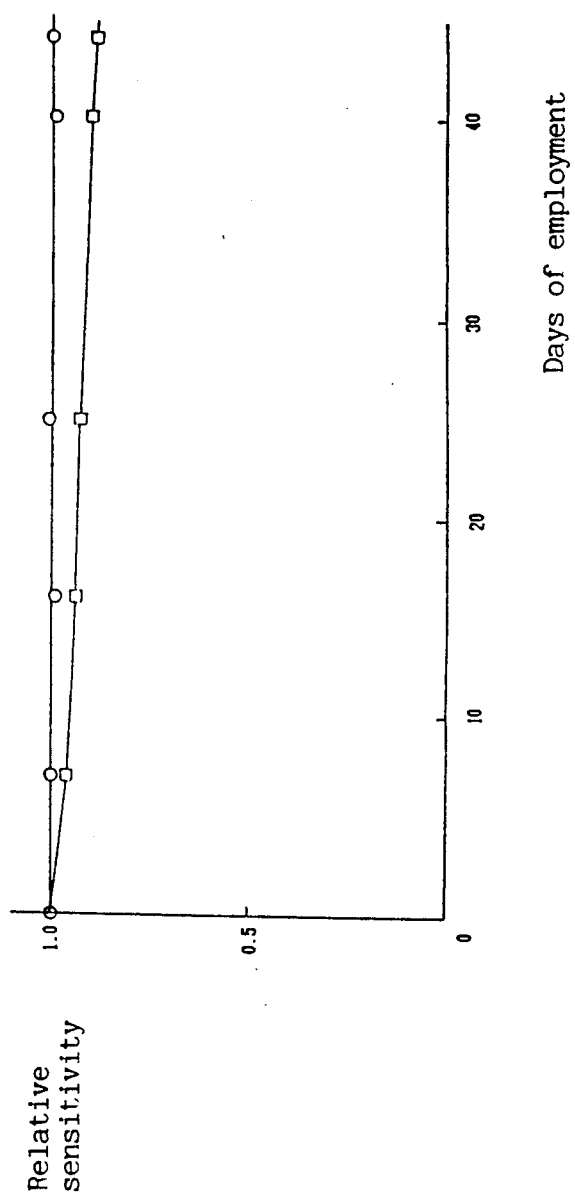
FIG. 4 is a graph illustrating the resultant improvement of the relative sensitivity against employment period of an alcohol concentration sensor in accordance with this invention.

FIG. 4 illustrates the results of the alcohol concentration sensor in accordance with the first embodiment of this invention. The graph illustrates the depression of the relative sensitivity vs. the days during which the sensor was employed. The line connecting white circles indicates the results of this embodiment, while the line connecting white squares indicates the results of the prior art.

SECOND EMBODIMENT

This embodiment is an improvement of the first embodiment and is developed to correct a potential error inevitable in the first embodiment, the potential error being caused by the reason why the gas sensor 27 is actually a thermometer for example a semiconductor type thermometer or a catalytic type thermometer.

To remove this drawback, an air temperature sensor (not shown), a temperature rise sensing means (not shown) and a temperature rise/alcohol concentration calibration means (not shown) are further provided.

Since the temperature rise correctly represents the heat emitted by oxidization of alcohol, the output of the temperature rise/alcohol concentration calibration means (not shown) indicates much more correct amount rather than that of the first embodiment.

THIRD EMBODIMENT

This embodiment is also an improvement of the first embodiment and is developed to correct a potential error inevitable in the first embodiment, the potential error being caused by the reason why the gas sensor 27 is actually a thermometer for example a semiconductor type thermometer or a catalytic type thermometer.

Figure 5:
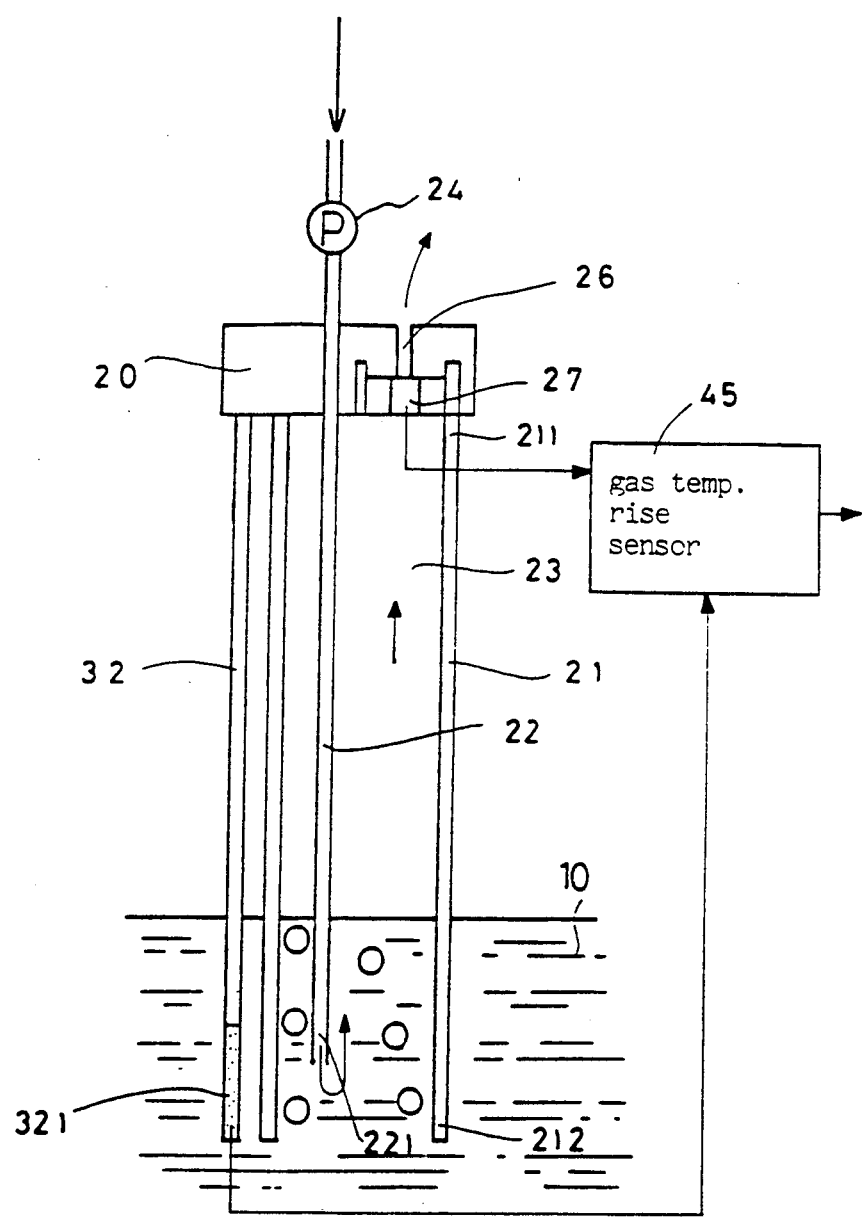
FIG. 5 is an alcohol concentration sensor in accordance with the third embodiment of this invention.

Referring to FIG. 5, the top end 211 of a tube shaped means 21 is closed with a top end closing means 20 and the bottom end 212 thereof is remained open, remaining an open space 23 therebetween. The bottom end 212 is soaked in the water 10 containing alcohol. An air supply tube 22 which is provided with a blower 24 penetrates the top end closing means 20 to extend into the water 10 containing alcohol. A gas sensor 27 is arranged in the top end closing means 20 to allow the gas mixture of the air and alcohol vapor flown out of the open space 23 of the tube shaped means 21.

In addition, a liquid temperature sensing means 32 extends downward from the top end closing means 20 to the neighborhood of the lower end 221 of the tube shaped means 21. A thermometer 321 is arranged at the lower end of the liquid temperature sensing means 32.

A gas temperature rise sensing means 45 which is input the gas temperature sensed by the gas sensor 27 and the liquid temperature sensed by the liquid temperature sensing means 32, are provided to determine the temperature rise correctly representing the heat emitted by oxidization of alcohol.

Being input the output of the gas temperature rise sensing means 45, a temperature rise/alcohol concentration calibration means (not shown) determines the alcohol concentration contained in the water 10.

FOURTH EMBODIMENT

This embodiment is an improvement of the second or third embodiment and is developed to correct an error caused by a variation of the resistance of the gas or liquid pass including the tube shaped means 21, the gas supply tube means 22, gas draw out means 26, and the like.

Figure 6:
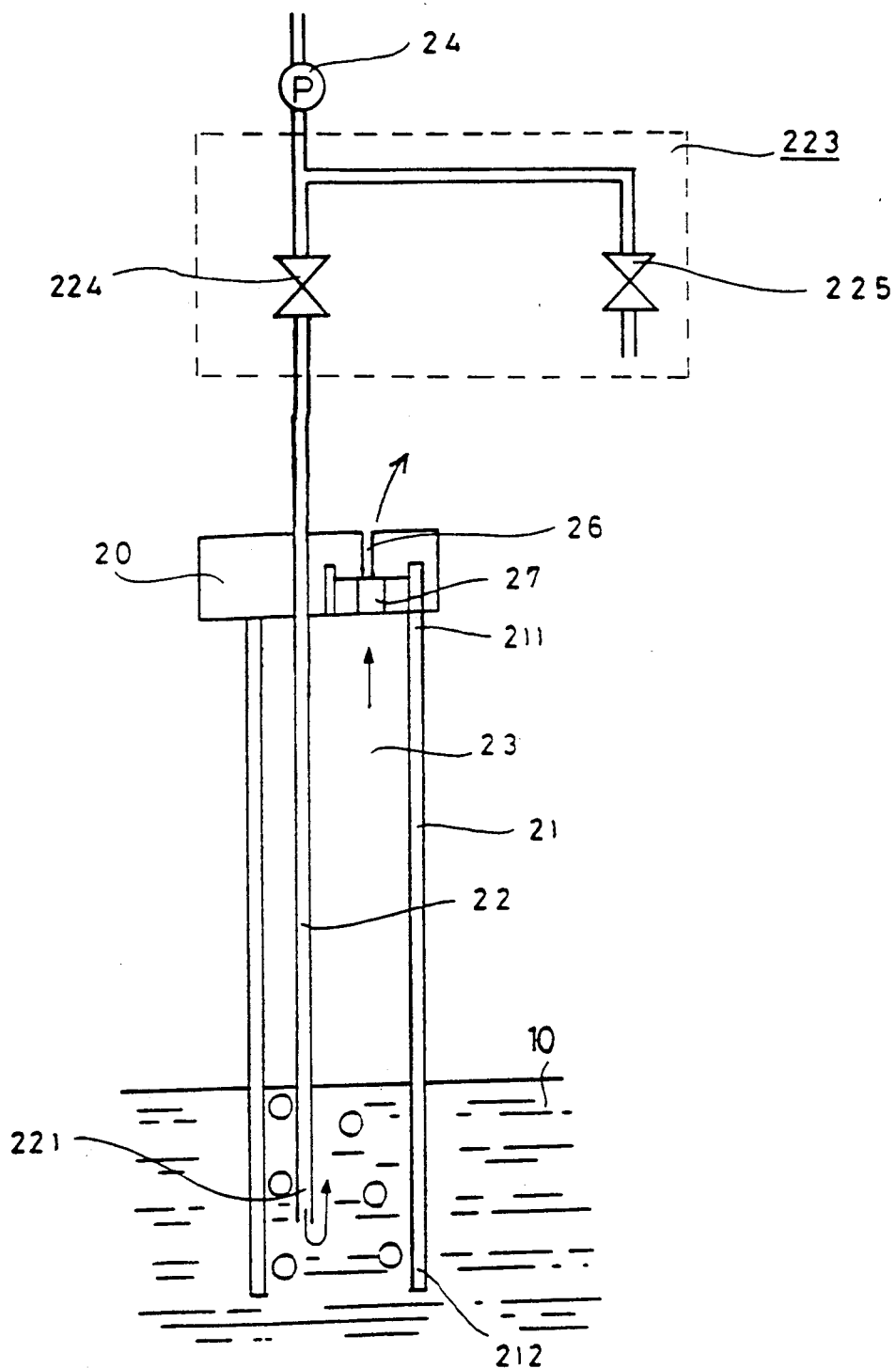
FIG. 6 is an alcohol concentration sensor in accordance with the fourth embodiment of this invention.

Referring to FIG. 6, the top end 211 of a tube shaped means 21 is closed with a top end closing means 20 and the bottom end 212 thereof is remained open, remaining an open space 23 therebetween. The bottom end 212 is soaked in the water 10 containing alcohol of which the alcohol concentration is examined. An air supply tube 22 which is provided with a blower 24 penetrates the top end closing means 20 to extend into the water 10 containing alcohol. A gas sensor 27 is arranged in the top end closing means 20 to allow the gas mixture of the air and alcohol vapor flown out of the open space 23 of the tube shaped means 21.

In addition, the gas supply tube means 22 is provided a flow stabilizing means 223.

The flow stabilizing means 223 generally could be a combination of a main valve 224 arranged in the gas supply tube means 22 proper and an additional valve 225 arranged in a branch of the gas supply tube means 22.

Figure 7:
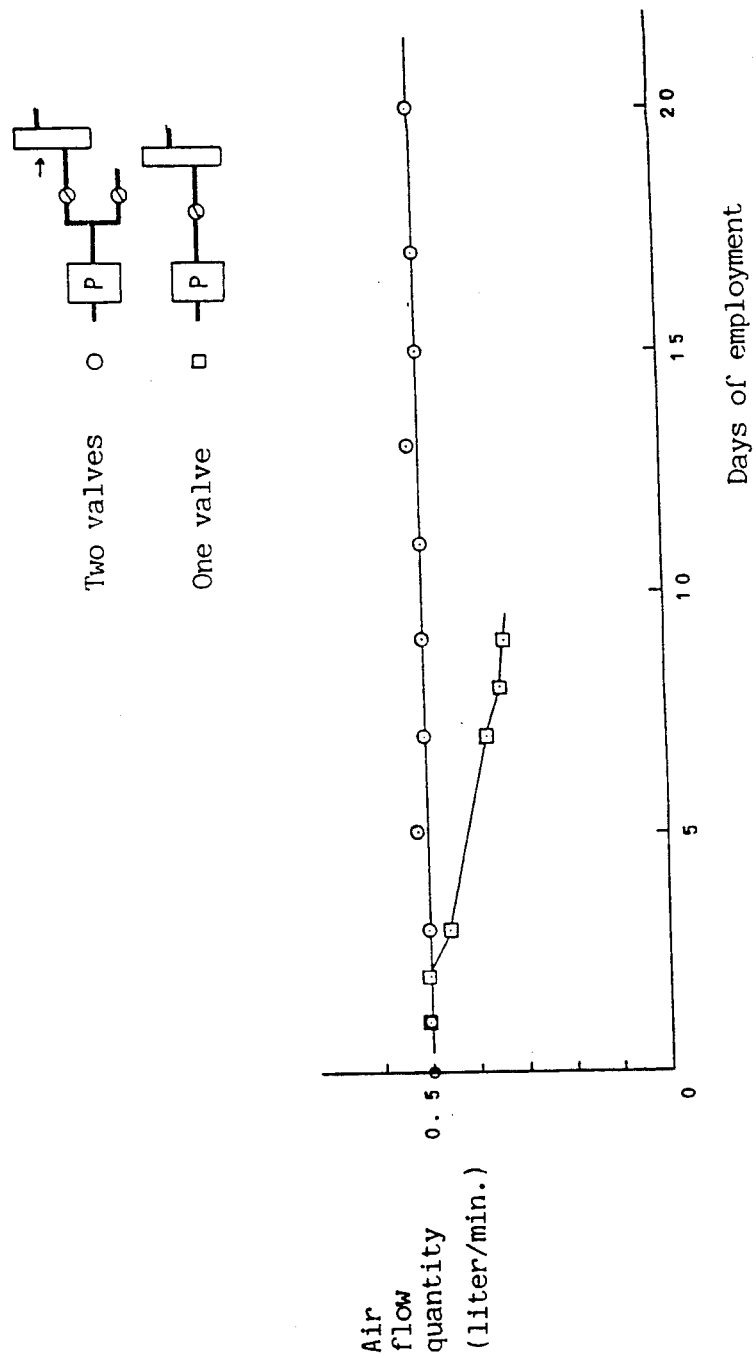
FIG. 7 is a graph illustrating the results of the flow stabilizing means provided the fourth embodiment of this invention.

FIG. 7 illustrates the results of the alcohol concentration sensor in accordance with the fourth embodiment of this invention. The graph illustrates the depression of the air flow vs. the days during which the sensor was employed. The line connecting white squares indicates the results of the case in which the main valve 224 alone is provided. The line connecting white circles indicates the results of the case in which another valve 225 is additionally provided to a branch attached to the main flow circuit of the gas supply tube means 22.

It is needless to emphasize that this fourth embodiment can be provided an air temperature sensing means for sensing the temperature of the environmental air, a gas temperature rise sensing means for determining the temperature rise of the gas mixture in the neighborhood of the gas oxidization means with respect to the ambient temperature determined by the air temperature sensing means, a temperature rise/alcohol concentration calibration means for calibrating the temperature rise to the corresponding alcohol concentration.

Further, this fourth embodiment can be provided a liquid temperature sensing means 32 which extends downward from the top end closing means 20 of the tube shaped means 21 to extend to the neighborhood of the lower end 221 of the tube shaped means 21 and which is provided a thermometer 321 at the lower end, a gas temperature rise sensing means 45 for determining the temperature rise by comparing the gas temperature and the liquid temperature, a temperature rise/alcohol concentration calibration means for calibrating the temperature rise to the corresponding alcohol concentration.

FIFTH EMBODIMENT

This embodiment is also an improvement of the second or third embodiment and is developed to correct an error caused by a variation of the resistance or the pressure of the liquid and/or gas pass including the tube shaped means 21, the gas supply tube means 22, gas draw out means 26, and the like.

Figure 8:
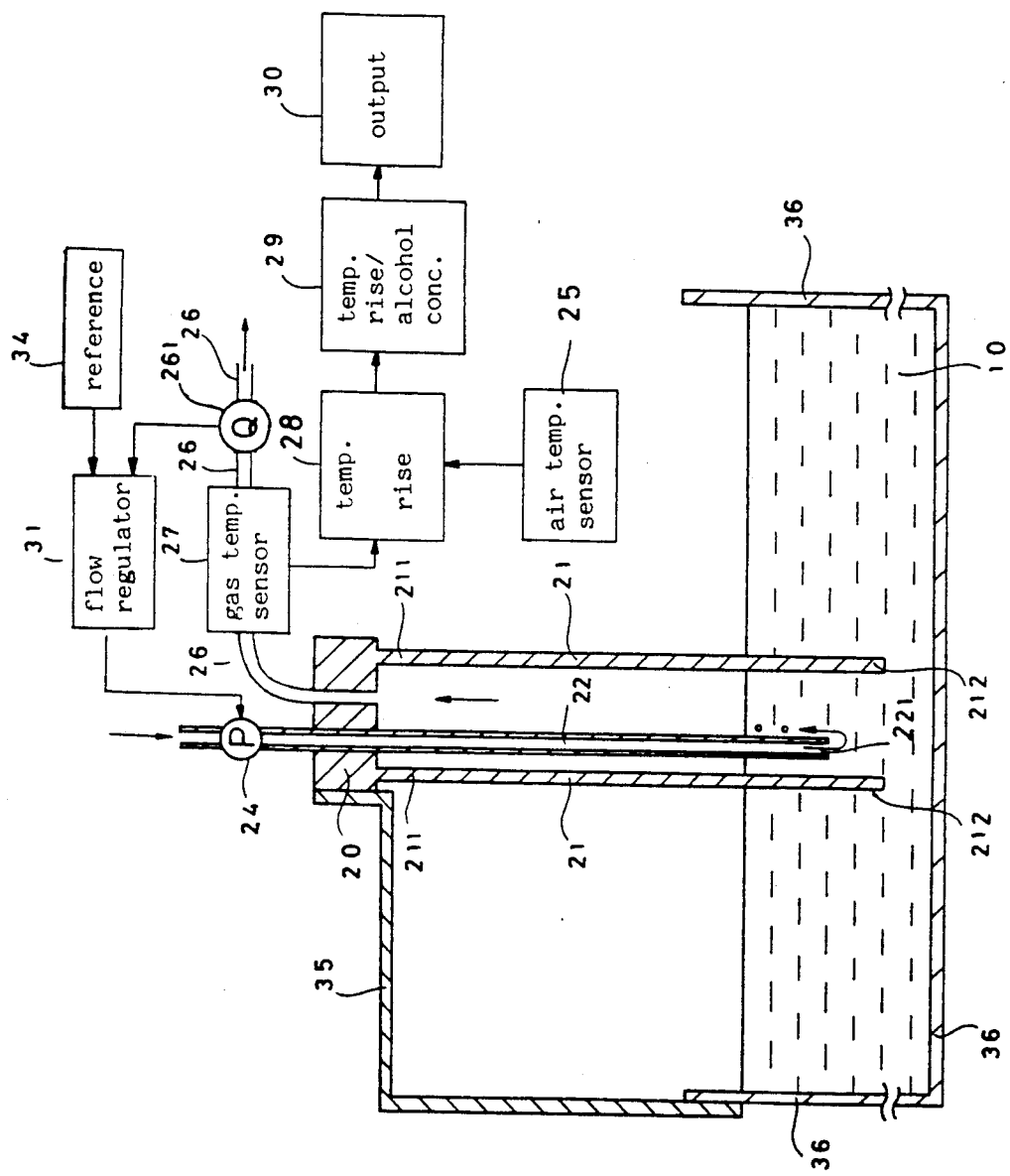
FIG. 8 is an alcohol concentration sensor in accordance with the fifth embodiment of this invention.

Referring to FIG. 8, the top end 211 of a tube shaped means 21 is closed with a top end closing means 20 and the bottom end 212 thereof is remained open, remaining an open space 23 therebetween. The bottom end 212 is soaked in the water 10 containing alcohol. An air supply tube means 22 which is provided with a blower 24 penetrates the top end closing member 20 to extend into the water 10 containing alcohol. A gas sensor 27 is arranged in the top end closing member 20 to allow the mixture of the air and alcohol vapor flown out of the open space 23 of the tube shaped means 21.

The output of the gas sensor 27 and the output of an ambient temperature sensing means 25 are input to a gas temperature rise sensing means 28 for determining the temperature rise of the gas in the neighborhood of the gas oxidization means (not shown) against the ambient temperature determined by the air temperature sensing means 25.

The output temperature rise of the gas temperature rise sensing means 28 is input to a temperature rise/alcohol concentration calibration means 29 and is calibrated to the corresponding alcohol concentration, before being output from an alcohol concentration output means 30.

Further, the output of a gas flow sensing means 261 is input to a gas flow regulation means 31 to be compared with a predetermined reference 34, for the ultimate purpose to keep the air flow to be supplied through the air supply tube means 22 at a predetermined amount.

The water 10 containing alcohol is storaged in a vessel 36 which supports the top end closing member 20 of the alcohol concentration sensor in accordance with this invention by means of a support 35.

Since this embodiment employs an automatic air flow regulation system, the air flow to be supplied through the air supply tube means 22 can be precisely regulated at a preferable amount.

SIXTH EMBODIMENT

Figure 9:
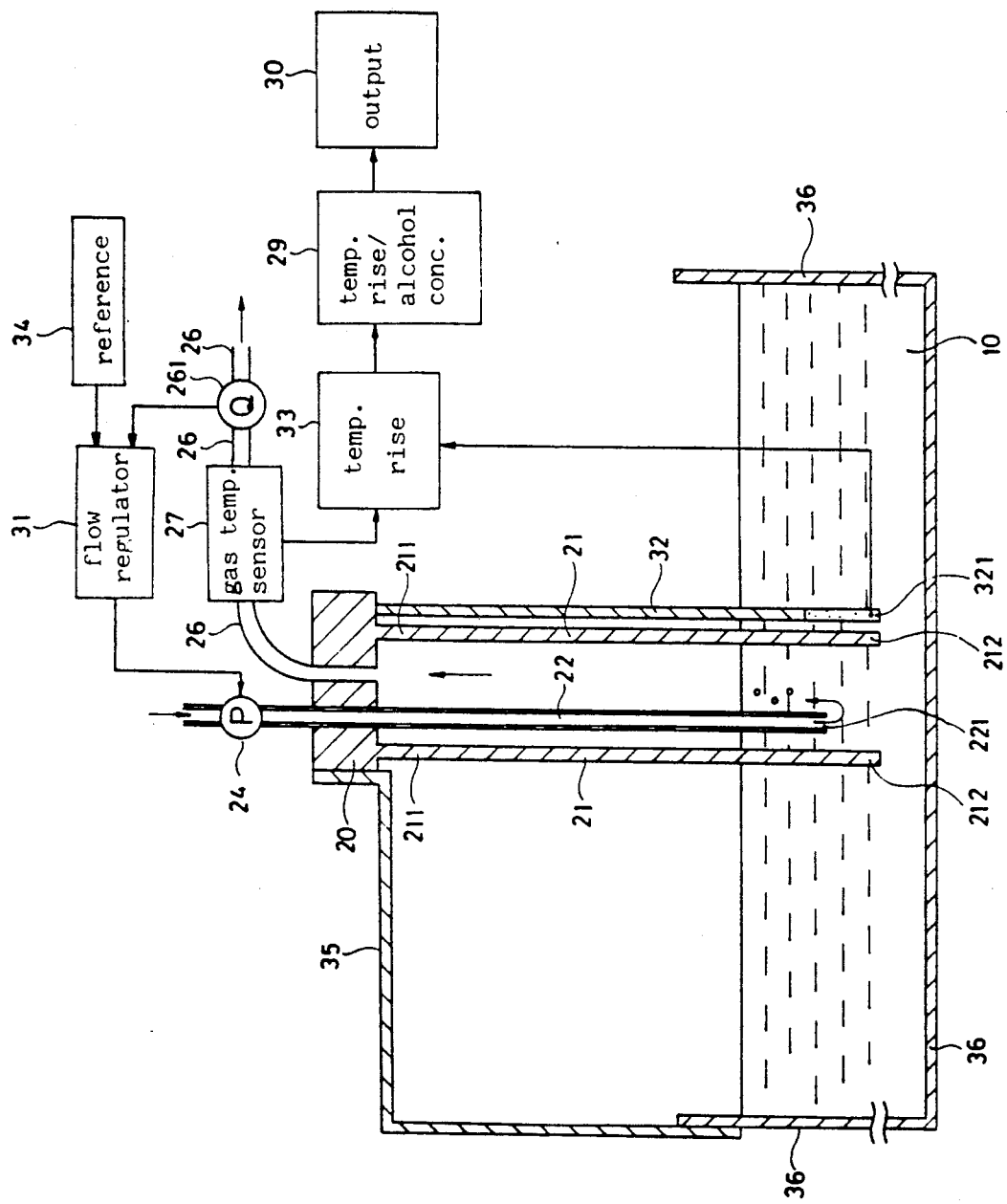
FIG. 9 is an alcohol concentration sensor in accordance with the sixth embodiment of this invention.

As is illustrated in FIG. 9, this embodiment is a combination of the third embodiment and the fifth embodiment. Therefore, the structure and results are also a combination of those of the third embodiment and the fifth embodiment.

For the purpose to avoid redundancy a detailed description of the structure is omitted, because it will be clear from the description referring to FIGS. 5 and 8.

SEVENTH EMBODIMENT

This is an embodiment in which an error caused by an unstable flow caused by explosion of the air bubbles at the natural surface of the water containing alcohol 10 is removed.

Figure 10:
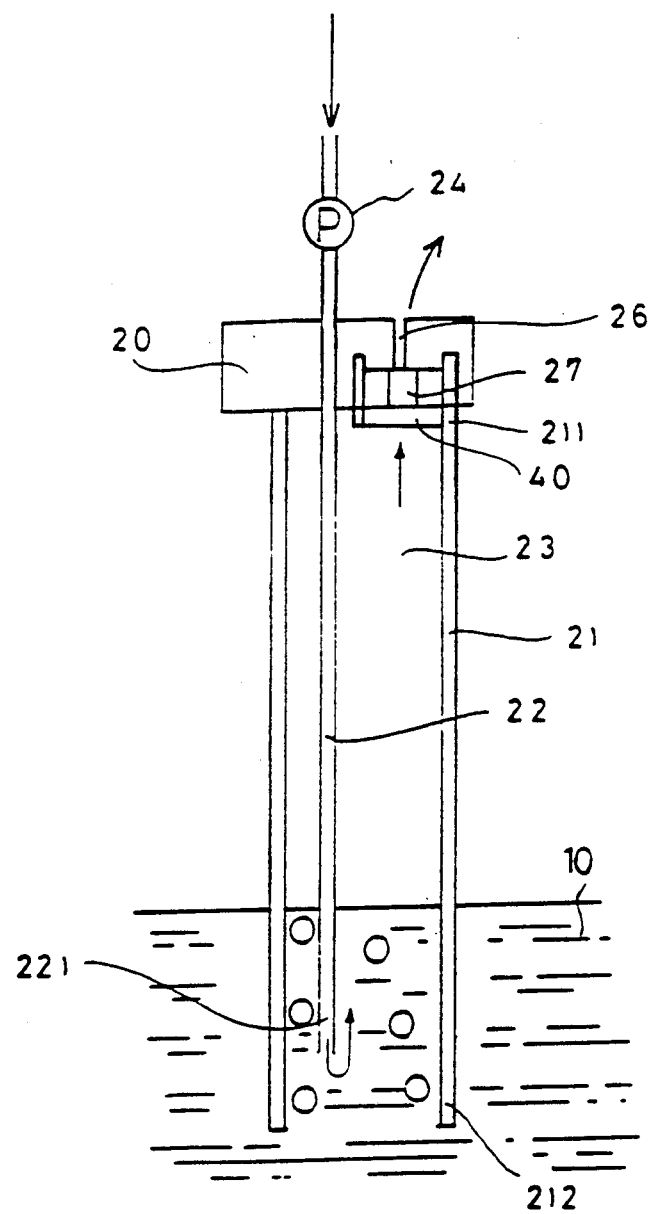
FIG. 10 is an alcohol concentration sensor in accordance with the seventh embodiment of this invention.

Referring to FIG. 10, the top end 211 of a tube shaped means 21 is closed with a top end closing member 20 and the bottom end 212 thereof is remained open, remaining an open space 23 therebetween. The bottom end 212 is soaked in the water 10 containing alcohol. An air supply tube 22 which is provided with a blower 24 penetrates the top end closing member 20 to the extend into the water 10 containing alcohol. A gas sensor 27 is arranged in the top end closing member 20 to allow the mixture of the air and alcohol vapor flown out of the open space 23 of the tube shaped means 21.

In addition, a filter 40 is arranged in the upstream of the gas temperature sensing means 27. Therefore, a rippled flow caused by eruption of the air bubbles at the natural surface of the water containing alcohol 10 is connected to a uniform flow, before it is flown into the gas temperature sensing means 27, resultantly causing the oxidization of alcohol to become uniform and enhancing the accuracy in the determined temperature and resultantly the determined alcohol concentration.

It is needless to emphasize that this seventh embodiment can be provided an air temperature sensing means 25 for sensing the temperature of the environmental air, a gas temperature rise sensing means 28 for determining the temperature rise of the gas in the neighborhood of the gas oxidization means with respect to the ambient temperature determined by the air temperature sensing means 25, a temperature rise/alcohol concentration calibration means 28 for calibrating the temperature rise to the corresponding alcohol concentration.

Further, this seventh embodiment can be provided a liquid temperature sensing means 32 which extends downward from the top end closing member 20 of the tube shaped means 21 to extend to the neighborhood of the lower end 221 of the tube shaped member 21 and which is provided a thermometer 321 at the lower end, a gas temperature rise sensing means 45 for determining the temperature rise by comparing the gas temperature and the liquid temperature, a temperature rise/alcohol concentration calibration means for calibrating the temperature rise to the corresponding alcohol concentration.

EIGHTH EMBODIMENT

This is an embodiment developed for the purpose to protect the gas temperature sensing means 27, resultantly enhancing the accuracy in the determined alcohol concentration.

Figure 11:
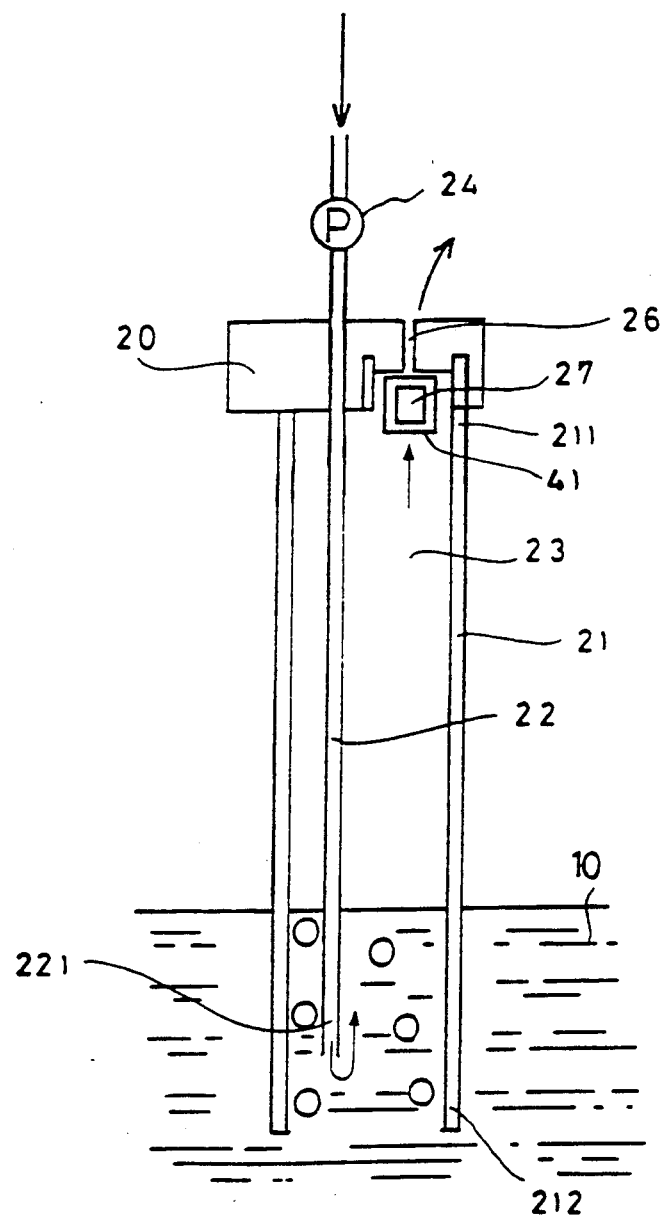
FIG. 11 is an alcohol concentration sensor in accordance with the eighth embodiment of this invention.

Referring to FIG. 11, the top end 211 of a tube shaped means 21 is closed with a top end closing member 20 and the bottom end 212 thereof is remained open, remaining an open space 23 therebetween. The bottom end 212 is soaked in the water 10 containing alcohol. An air supply tube 22 which is provided with a blower 24 penetrates the top end closing member 20 to extend into the water 10 containing alcohol. A gas sensor 27 is arranged in the top end closing member 20 to allow the mixture of the air and alcohol vapor flown out of the open space 23 of the tube shaped means 21.

In addition, the gas temperature sensing means 27 is covered by a porous film 41 which allows the air to pass through but prevents water from passing through and is resistive against heat.

It is needless to emphasize that this eighth embodiment can be provided an air temperature sensing means 25 for sensing the temperature of the environmental air, a gas temperature rise sensing means 28 for determining the temperature rise of the gas in the neighborhood of the gas oxidization means with respect to the ambient temperature determined by the air temperature sensing means 25, a temperature rise/alcohol concentration calibration means 28 for calibrating the temperature rise to the corresponding alcohol concentration.

Further, this eighth embodiment can be provided a liquid temperature sensing means 32 which extends downward from the top end closing member 20 of the tube shaped means 21 to extend to the neighborhood of the lower end 221 of the tube shaped member 21 and which is provided a thermometer 321 at the lower end, a gas temperature rise sensing means 45 for determining the temperature rise by comparing the gas temperature and the liquid temperature, a temperature rise/alcohol concentration calibration means for calibrating the temperature rise to the corresponding alcohol concentration.

NINTH EMBODIMENT

All the foregoing alcohol concentration sensors must be held by some supporting member, as illustrated in FIGS. 8 and 9. This causes an error for the determined alcohol concentration due to the depth of the liquid of which the alcohol concentration is examined.

This is an embodiment developed for the purpose to enable the alcohol concentration sensor to keep an excellent accuracy, regardless of the depth of the liquid of which the alcohol concentration is examined.

Figure 12:
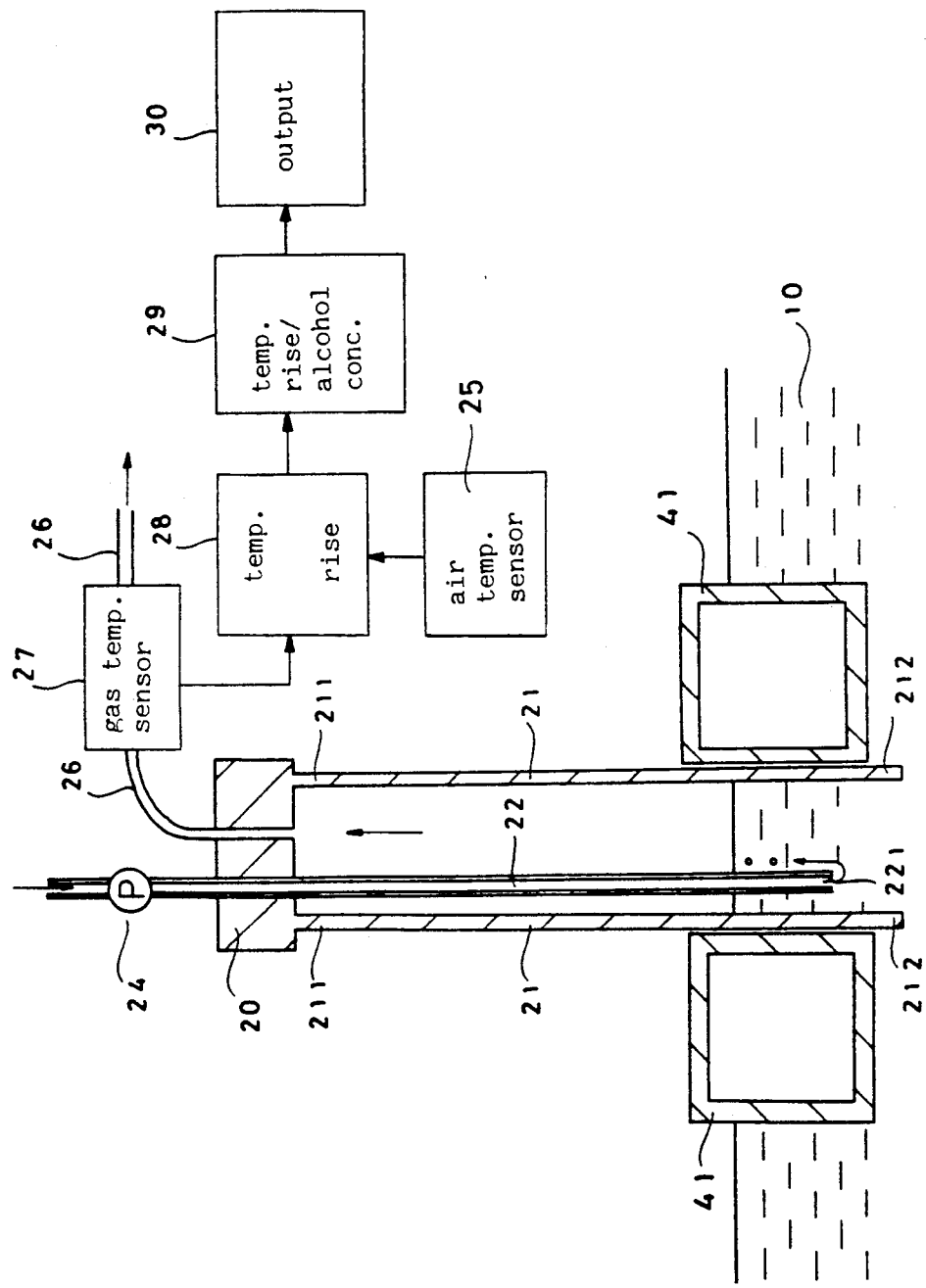
FIG. 12 is an alcohol concentration sensor in accordance with the ninth embodiment of this invention.

Referring to FIG. 12, the top end 211 of a tube shaped means 21 is closed with a top end closing member 20 and the bottom end 212 thereof is remained open, remaining an open space 23 therebetween. The bottom end 212 is soaked in the water 10 containing alcohol. An air supply tube 22 which is provided with a blower 24 penetrates the top end closing member 20 to extend into the water 10 containing alcohol. A gas sensor 27 is arranged in the top end closing member 20 to allow the mixture of the air and alcohol vapor flown out of the open space 23 of the tube shaped means 21.

The output of the gas sensor 27 and the output of an ambient temperature sensing means 25 are input to a gas temperature rise sensing means 28 for determining the temperature rise of the gas in the neighborhood of the gas oxidization means (not shown) against the ambient temperature determined by the air temperature sensing means 25.

The output temperature rise of the gas temperature rise sensing means 28 is input to a temperature rise/alcohol concentration calibration means 29 and is calibrated to the corresponding alcohol concentration, before being output from an alcohol concentration output means 30.

In addition, a float 41 is arranged surrounding the tube shaped means 21.

Since the float 41 is arranged surrounding the tube shaped means 21, this alcohol concentration sensor is allowed to be employed, regardless of the depth of the liquid of which the alcohol concentration is examined, maintaining a satisfactory magnitude of accuracy.

Figure 13:
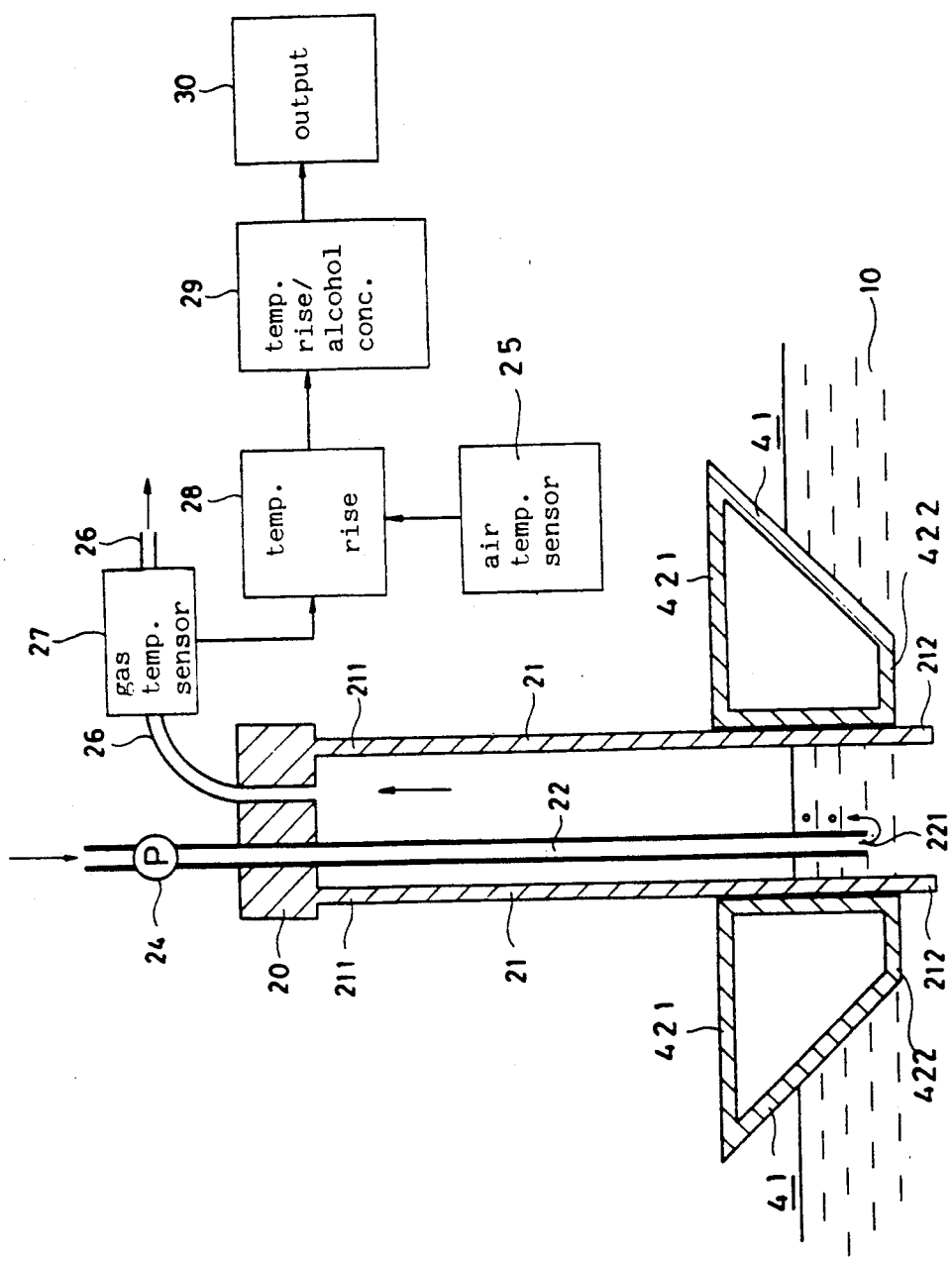
FIG. 13 is an alcohol concentration sensor in accordance with a modification of the ninth embodiment of this invention.

For the purpose to enhance the dynamic stability or the force of restitution, it is effective to make the surrounding length of the external upper edge 421 larger than the surrounding length of the internal lower edge 422, as illustrated in FIG. 13.

TENTH EMBODIMENT

Figure 14:
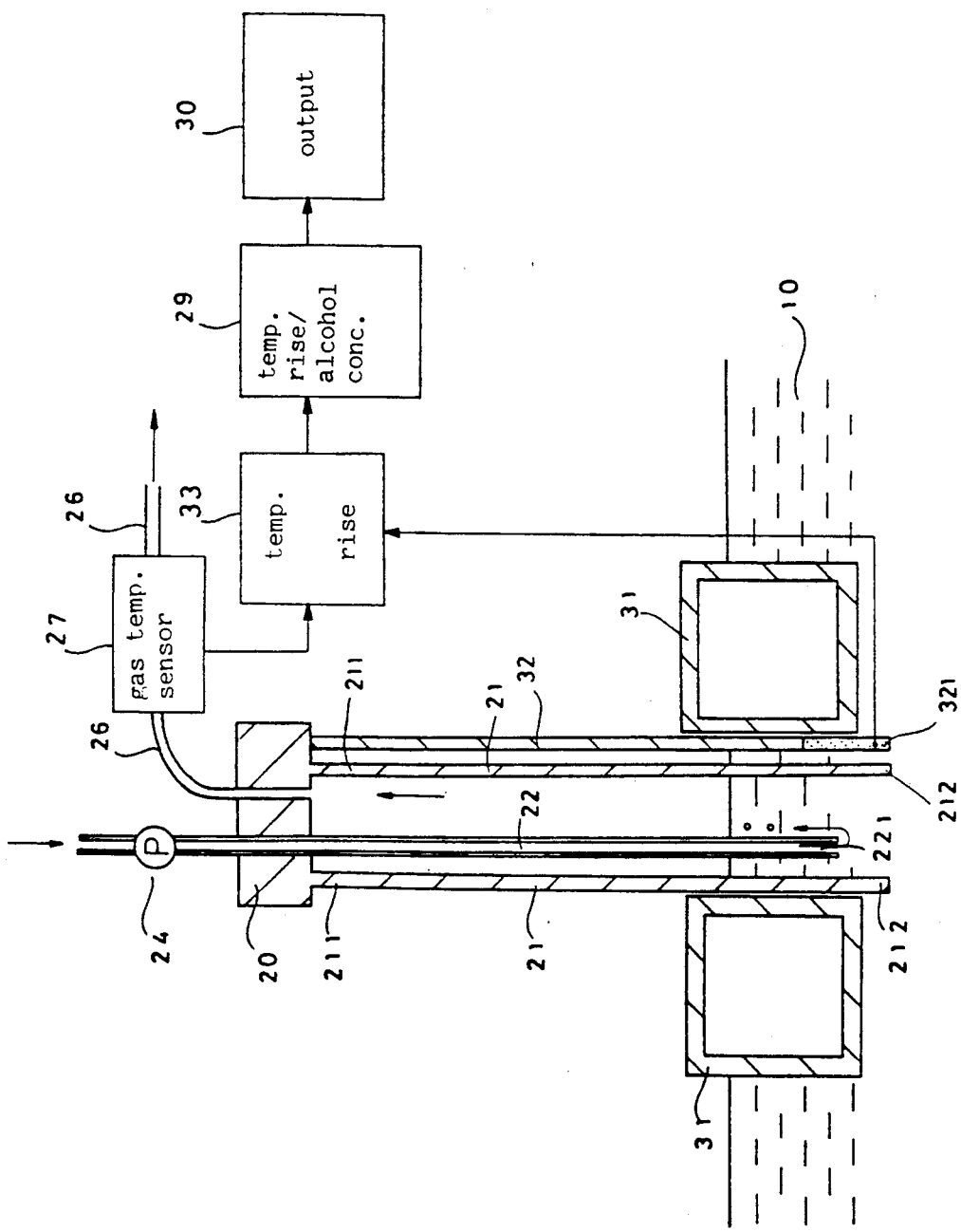
FIG. 14 is an alcohol concentration sensor in accordance with the tenth embodiment of this invention.

As is illustrated in FIG. 14, this embodiment is a combination of the ninth embodiment and the third embodiment developed for the purpose to enhance the accuracy, regardless of a variation of the liquid temperature. In other words, this embodiment is a combination of the third embodiment and the tenth embodiment.

For the purpose to avoid redundancy, a detailed description of the structure is omitted, because it will be clear from the description referring to FIGS. 3 and 12.

Illustrated in FIG. 15 is a modification of the alcohol concentration sensor in accordance with the tenth embodiment illustrated in FIG. 14 developed for the purpose to enhance the dynamic stability of the force of restitution, such improvement is realized by making the surrounding length of the external upper edge 311 larger than the surrounding length of the internal lower edge 312.

What is claimed is:

1. An alcohol concentration sensor comprising:
   a tubular member having a top end closing means for closing a top end portion of the tubular member, and wherein the bottom end of the tubular member remains open;
   a gas supply tube means which penetrates said top end closing means to extend down into said tubular member, wherein said gas supply tube means is provided with an air blower means, and having the lower end thereof terminate slightly higher than the bottom end of said tubular member, wherein said lower end of said gas supply tube means is soaked into a liquid containing water and alcohol, of which the alcohol concentration is required to be determined, deeply sufficient to allow the air bubbles flown out of the gas supply tube means into said liquid to absorb sufficient quantity of alcohol contained in said liquid, whenever said tubular member is soaked in said liquid;
   a gas drawing out means for drawing out gas from said liquid, wherein said gas drawing out means penetrates said top end closing means;
   a gas temperature sensing means connected to said gas drawing out means, said gas temperature sensing means having a a gas oxidization means, wherein said temperature sensing means determines the temperature of the gas in the neighborhood of the gas oxidization means for oxidizing the alcohol evaporated from said liquid;
   a temperature/alcohol concentration calibration means for calibrating said temperature of the gas toward the corresponding alcohol concentration; and
   an alcohol concentration output means for outputting the alcohol concentration determined by said temperature/alcohol concentration calibration means.

2. An alcohol concentration sensor comprising:
   a tubular member having a top end closing means for closing a top end portion of the tubular member, and wherein the bottom end of the tubular member remains open;
   a gas supply tube means which penetrates said top end closing means to extend down into said tubular member, wherein said gas supply tube means is provided with an air blower means, and having the lower end thereof terminate slightly higher than the bottom end of said tubular member, wherein said lower end of said gas supply tube means is soaked into a liquid containing water and alcohol, of which the alcohol concentration is required to be determined, deeply sufficient to allow the air bubbles flown out of the gas supply tube means into said liquid to absorb sufficient quantity of alcohol contained in said liquid, whenever said tubular member is soaked in said liquid;
   a gas drawing out means for drawing out gas from said liquid, wherein said gas drawing out means penetrates said top end closing means;
   a gas temperature sensing means connected to said gas drawing out means, said gas temperature sensing means having a a gas oxidization means, wherein said temperature sensing means determines the temperature of the gas in the neighborhood of the gas oxidization means for oxidizing the alcohol evaporated from said liquid;
   an air temperature sensing means for sensing the temperature of the environmental air;
   a gas temperature rise sensing means for determining the temperature rise of said gas in the neighborhood of the gas oxidation means against the ambient temperature determined by said gas temperature sensing means;
   a temperature rise/alcohol concentration calibration means for calibrating said temperature rise toward the corresponding alcohol concentration; and
   an alcohol concentration output means for outputting the alcohol concentration determined by said temperature rise/alcohol concentration calibration means.

3. An alcohol concentration sensor comprising:
   a tubular member having a top end closing means for closing a top end portion of the tubular member, and wherein the bottom end of the tubular member remains open;
   a gas supply tube means which penetrates said top end closing means to extend down into said tubular member, wherein said gas supply tube means is provided with an air blower means, and having the lower end thereof terminate slightly higher than the bottom end of said tubular member, wherein said lower end of said gas supply tube means is soaked into a liquid containing water and alcohol, of which the alcohol concentration is required to be determined, deeply sufficient to allow the air bubbles flown out of the gas supply tube means into said liquid to absorb sufficient quantity of alcohol contained in said liquid, whenever said tubular member is soaked in said liquid;
   a gas drawing out means for drawing out gas from said liquid, wherein said gas drawing out means penetrates said top end closing means;
   a gas temperature sensing means connected to said gas drawing out means, said gas temperature sensing means having a a gas oxidization means, wherein said temperature sensing means determines the temperature of the gas in the neighborhood of the gas oxidization means for oxidizing the alcohol evaporated from said liquid; p1 a liquid temperature sensing means for sensing the temperature of the liquid, wherein the liquid temperature sensing means extends downward from said top end closing member to the neighborhood of said lower end of said tubular member and includes a thermometer at the lower end thereof;
   a gas temperature rise sensing means for determining the temperature rise by comparing said gas temperature and said liquid temperature;
   a temperature rise/alcohol concentration calibration means for calibrating said temperature rise to the corresponding alcohol concentration; and an alcohol concentration output means for outputting the alcohol concentration determined by said temperature rise/alcohol concentration calibration means.

4. An alcohol concentration sensor comprising:
a tubular member having a top end closing means for closing a top end portion of the tubular member, and wherein the bottom end of the tubular member remains open;
a gas supply tube means having a flow stabilizing means which penetrates said top end closing means to extend down into said tubular member, wherein said gas supply tube means is provided with an air blower means, having the lower end thereof terminate slightly higher than the bottom end of said tubular member, wherein said lower end of said gas supply tube means is soaked into a liquid containing water and alcohol, of which the alcohol concentration is required to be determined, deeply sufficient to allow the air bubbles flown out of the gas supply tube means into said liquid to absorb sufficient quantity of alcohol contained in said liquid, whenever said tubular member is soaked in said liquid;
a gas drawing out means for drawing out gas from said liquid, wherein said gas drawing out means penetrates said top end closing means;
a gas temperature sensing means connected to said gas drawing out means, said gas temperature sensing means having a a gas oxidization means, wherein said temperature sensing means determines the temperature of the gas in the neighborhood of the gas oxidization means for oxidizing the alcohol evaporated from said liquid;
a temperature/alcohol concentration calibration means for calibrating said temperature of the gas toward the corresponding alcohol concentration; and
an alcohol concentration output means for outputting the alcohol concentration determined by said temperature/alcohol concentration calibration means.

5. An alcohol concentration sensor in accordance with claim 4, wherein said flow stabilizing means is a valve arranged in said gas supply means.

6. An alcohol concentration sensor in accordance with claim 4, wherein said flow stabilizing means is a combination of a valve arranged in said gas supply means and an additional valve arranged in a branch of said gas supply tube means.

7. An alcohol concentration sensor comprising:
a tubular member having a top end closing means for closing a top end portion of the tubular member, and wherein the bottom end of the tubular member remains open;
a gas supply tube means which penetrates said top end closing means to extend down into said tubular member, wherein said gas supply tube means is provided with an air blower means, and having the lower end thereof terminate slightly higher than the bottom end of said tubular member, wherein said lower end of said gas supply tube means is soaked into a liquid containing water and alcohol, of which the alcohol concentration is required to be determined, deeply sufficient to allow the air bubbles flown out of the gas supply tube means into said liquid to absorb sufficient quantity of alcohol contained in said liquid, whenever said tubular member is soaked in said liquid;
a gas drawing out means for drawing out gas from said liquid, wherein said gas drawing out means penetrates said top end closing means;
a gas flow sensing means for sensing the flow of gas;
a gas flow regulation means for comparing the gas flow determined by said gas flow sensing means and a predetermined reference; and
a gas temperature sensing means connected to said gas drawing out means for determining the temperature of the gas in the neighborhood of a gas oxidizaiton means for oxidizing the alcohol evaporated from said liquid;
an ambient temperature sensing means for sensing the temperature of the environmental air;
a gas temperature rise sensing means for determining the temperature rise of said gas in the neighborhood of the gas oxidization means against said ambient temperature determined by said gas temperature sensing means;
a temperature rise/alcohol concentration calibration means for calibrating said temperature rise to the corresponding alcohol concentration;
an alcohol concentration output means for outputting the alcohol concentration determined by said temperature/alcohol concentration calibration means.

8. An alcohol concentration sensor comprising:
a tubular member having a top end closing means for closing a top end portion of the tubular member, and wherein the bottom end of the tubular member remains open;
a gas supply tube means which penetrates said top end closing means to extend down into said tubular member, wherein said gas supply tube means is provided with an air blower means, and having the lower end thereof terminate slightly higher than the bottom end of said tubular member, wherein said lower end of said gas supply tube means is soaked into a liquid containing water and alcohol, of which the alcohol concentration is required to be determined, deeply sufficient to allow the air bubbles flown out of the gas supply tube means into said liquid to absorb sufficient quantity of alcohol contained in said liquid, whenever said tubular member is soaked in said liquid;
a gas drawing out means for drawing out gas from said liquid, wherein said gas drawing out means penetrates said top end closing means;
a gas flow sensing means for sensing the flow of gas;
a gas flow regulation means for comparing the gas flow determined by said gas flow sensing means and a predetermined reference;
a gas temperature sensing means connected to said gas drawing out means for determining the temperature of the gas in the neighborhood of a gas oxidizaiton means for oxidizing the alcohol evaporated from said liquid;
a liquid temperature sensing means which extends downward from said top end closing means to extend to the neighborhood of said lower end of said tubular member and which has a thermometer at the lower end thereof;
a gas temperature rise sensing means for determining the temperature rise by comparing the gas temperature determined by said gas temperature sensing means and the liquid temperature determined by said thermometer;

a temperature rise/alcohol concentration calibration means for calibrating said temperature rise to the corresponding alcohol concentration; and an alcohol concentration output means for outputting the alcohol concentration determined by the temperature/alcohol concentration calibration means.

9. An alcohol concentration sensor comprising:

a tubular member having a top end closing means for closing a top end portion of the tubular member, and wherein the bottom end of the tubular member remains open;

a gas supply tube means which penetrates said top end closing means to extend down into said tubular member, wherein said gas supply tube means is provided with an air blower means, and having the lower end thereof terminate slightly higher than the bottom end of said tubular member, wherein said lower end of said gas supply tube means is soaked into a liquid containing water and alcohol, of which the alcohol concentration is required to be determined, deeply sufficient to allow the air bubbles flown out of the gas supply tube means into said liquid to absorb sufficient quantity of alcohol contained in said liquid, whenever said tubular member is soaked in said liquid;

a gas drawing out means for drawing out gas from said liquid, wherein said gas drawing out means penetrates said top end closing means and which has a filter for filtering water particles;

a gas temperature sensing means connected to said gas drawing out means, said gas temperature sensing means having a gas oxidization means, wherein said temperature sensing means determines the temperature of the gas in the neighborhood of the gas oxidizaiton means for oxidizing the alcohol evaporated from said liquid;

a temperature/alcohol concentration calibration means for calibrating said temperature of the gas toward the corresponding alcohol concentration; and an alcohol concentration output means for outputting the alcohol concentration determined by said temperature/alcohol concentration calibration means.

10. An alcohol concentration sensor comprising:

a tubular member having a top end closing means for closing a top end portion of the tubular member, and wherein the bottom end of the tubular member remains open;

a gas supply tube means which penetrates said top end closing means to extend down into said tubular member, wherein said gas supply tube means is provided with an air blower means, and having the lower end thereof terminate slightly higher than the bottom end of said tubular member, wherein said lower end of said gas supply tube means is soaked into a liquid containing water and alcohol, of which the alcohol concentration is required to be determined, deeply sufficient to allow the air bubbles flown out of the gas supply tube means into said liquid to absorb sufficient quantity of alcohol contained in said liquid, whenever said tubular member is soaked in said liquid;

a gas drawing out means for drawing out gas from said liquid, wherein said gas drawing out means penetrates said top end closing means;

a gas temperature sensing means connected to said gas drawing out means and protected by a porous film which allows the air to pass through but prevents water from passing through and is resistive against heat.

11. An alcohol concentration sensor comprising:

a tubular member having a top end closing means for closing a top end portion of the tubular member, and wherein the bottom end of the tubular member remains open;

a gas supply tube means which penetrates said top end closing means to extend down into said tubular member, wherein said gas supply tube means is provided with an air blower means, and having the lower end thereof terminate slightly higher than the bottom end of said tubular member, wherein said lower end of said gas supply tube means is soaked into a liquid containing water and alcohol, of which the alcohol concentration is required to be determined, deeply sufficient to allow the air bubbles flown out of the gas supply tube means into said liquid to absorb sufficient quantity of alcohol contained in said liquid, whenever said tubular member is soaked in said liquid;

a gas drawing out means for drawing out gas from said liquid, wherein said gas drawing out means penetrates said top end closing means;

a gas temperature sensing means connected to said gas drawing out means, said gas temperature sensing means having a gas oxidization means, wherein said temperature sensing means determines the temperature of the gas in the neighborhood of the gas oxidizaiton means for oxidizing the alcohol evaporated from said liquid;

an ambient temperature sensing means for sensing the temperature of the environmental air;

a gas temperature rise sensing means for determining the temperature rise of the gas in the neighborhood of said gas oxidization means against the ambient temperature determined by said gas temperature sensing means;

a temperature rise/alcohol concentration calibration means for calibrating said temperature rise to the corresponding alcohol concentration;

an alcohol concentration output means for outputting the alcohol concentration determined by the temperature/alcohol concentration calibration means, and a float arranged surrounding said tubular member.

12. An alcohol concentration sensor in accordance with claim 11, wherein the length of the external upper edge of said float is larger than the length of the internal lower edge to thereby enhance the dynamical stability or the force of restitution.

13. An alcohol concentration sensor comprising:

a tubular member having a top end closing means for closing a top end portion of the tubular member, and wherein the bottom end of the tubular member remains open;

a gas supply tube means which penetrates said top end closing means to extend down into said tubular member, wherein said gas supply tube means is provided with an air blower means, and having the lower end thereof terminate slightly higher than the bottom end of said tubular member, wherein said lower end of said gas supply tube means is soaked into a liquid containing water and alcohol, of which the alcohol concentration is required to be determined, deeply sufficient to allow the air bubbles flown out of the gas supply tube means into said liquid to absorb sufficient quantity of alcohol contained in said liquid, whenever said tubular member is soaked in said liquid;

a gas drawing out means for drawing out gas from said liquid, wherein said gas drawing out means penetrates said top end closing means;

a gas temperature sensing means connected to said gas drawing out means, for determining the temperature of the gas in the neighborhood of the gas oxidizaiton means for oxidizing the alcohol evaporated from said liquid;

a liquid temperature sensing means which extends downward from said top end closing means to the neighborhood of said lower end of said tube shaped means and which has a thermometer at the lower end thereof;

a gas temperature rise sensing means for determining the temperature rise by comparing said gas temperature and said liquid temperature;

a temperature rise/alcohol concentration calibration means for calibrating said temperature rise to the corresponding alcohol concentration; and an alcohol concentration output means for outputting said alcohol concentration determined by said temperature rise/alcohol concentration calibration means, and a float arranged surrounding said tubular member.

14. An alcohol concentration sensor in accordance with claim 13, wherein the length of the external upper edge of said float is larger than the length of the internal lower edge to thereby enhance the dynamical stability or the force of restitution.

* * * * *